US008425440B2

(12) United States Patent
DeToro et al.

(10) Patent No.: US 8,425,440 B2
(45) Date of Patent: Apr. 23, 2013

(54) ORTHOTIC CAPABLE OF ACCEPTING REPLACEABLE SUPPORTS FOR A PIVOTING JOINT OF A HUMAN BODY (75) Inventors: William W. DeToro, Poland, OH (US); Brian S. Perala, Warren, OH (US); William A. DeToro, Poland, OH (US); Jack N. Huey, Poland, OH (US)

(73) Assignee: Anatomical Concepts, Inc., Poland, OH (US)

( * ) Notice: Subject to any disclaimer, the term of this patent is extended or adjusted under 35 U.S.C. 154(b) by 633 days.

(21) Appl. No.: 12/694,509

(22) Filed: Jan. 27, 2010

(65) Prior Publication Data

US 2010/0130900 A1  May 27, 2010

Related U.S. Application Data (63) Continuation-in-part of application No. 12/215,733, filed on Jun. 30, 2008, now Pat. No. 8,062,243.

(51) Int. Cl.
*A61F 5/00* (2006.01)

(52) U.S. Cl.
USPC ............... 602/16; 602/12; 602/23; 602/27; 602/28

(58) Field of Classification Search ............... 602/5, 12, 602/16, 23, 27–29; 16/265–266; 482/79–80; 36/117.1, 117.4, 118.2, 118.7, 118.8, 118.9, 36/140, 155–156, 158, 160
See application file for complete search history.

(56) References Cited

U.S. PATENT DOCUMENTS

| 230,491 A * | 7/1880 | Peer ........................... 16/266 |
| 1,332,047 A | 2/1920 | Lasher |
| 1,598,504 A | 8/1926 | Pierce et al. |
| 2,138,975 A * | 12/1938 | Malik ........................... 602/16 |
| 2,439,100 A | 4/1948 | Richards |
| 2,444,839 A | 7/1948 | Markkula |
| 2,525,237 A | 10/1950 | Park |
| 2,663,294 A | 12/1953 | Harrison |
| 2,847,991 A | 8/1958 | Andrews |
| 2,874,690 A | 2/1959 | Cowgill |
| 3,527,209 A | 9/1970 | Baker |
| 3,986,501 A | 10/1976 | Schad |
| 4,329,982 A | 5/1982 | Heaney |
| 4,566,447 A | 1/1986 | Deis |
| 4,651,723 A | 3/1987 | Satoh |
| 4,817,589 A | 4/1989 | Wertz |
| 5,052,076 A * | 10/1991 | Spaeth ........................... 16/266 |
| 5,088,479 A | 2/1992 | DeToro |
| 5,224,925 A | 7/1993 | Varn |
| 5,259,834 A | 11/1993 | Wittmeyer |
| 5,302,169 A | 4/1994 | Taylor |
| 5,382,224 A | 1/1995 | Spangler |
| 5,486,157 A | 1/1996 | DiBenedetto |
| 5,545,127 A | 8/1996 | DeToro |
| 5,593,383 A | 1/1997 | DeToro |

(Continued)

*Primary Examiner* — Patricia Bianco
*Assistant Examiner* — Kari Petrik
(74) *Attorney, Agent, or Firm* — Robert J. Herberger (57) ABSTRACT

An orthotic for a joint of the human body, at which a body part pivots, includes first and second hinge members able to extend along respective posterior portions of body parts near the joint. The second member is able to be fitted with alternate orthotic support portions. A hinge connection joins the first member and the second member, permitting angular motion about an axis, and mutual disconnection and reconnection of the members at the hinge connection as the second member pivots relative to the first member.

7 Claims, 9 Drawing Sheets

U.S. PATENT DOCUMENTS

| | | |
|---|---|---|
| 5,908,398 A | 6/1999 | DeToro |
| 5,944,679 A | 8/1999 | DeToro |
| 6,102,881 A | 8/2000 | Quackenbush et al. |
| 6,302,858 B1 | 10/2001 | DeToro et al. |
| 6,350,246 B1 | 2/2002 | DeToro et al. |
| 6,377,178 B1 | 4/2002 | DeToro et al. |
| 6,464,659 B1 | 10/2002 | DeToro et al. |
| 6,793,638 B1 | 9/2004 | DeToro et al. |
| 7,011,641 B1 | 3/2006 | DeToro et al. |
| 7,112,181 B1 | 9/2006 | DeToro et al. |
| 7,122,016 B1 | 10/2006 | DeToro et al. |
| 2010/0016772 A1 | 1/2010 | DeToro et al. |
| 2010/0016773 A1 | 1/2010 | DeToro et al. |

* cited by examiner

ORTHOTIC CAPABLE OF ACCEPTING REPLACEABLE SUPPORTS FOR A PIVOTING JOINT OF A HUMAN BODY

PRIORITY INFORMATION

The present application claims priority as a continuation-in-part of application having Ser. No. 12/215,733, now issued as U.S. Pat. No. 8,062,243, which was filed in the United States on Jun. 30, 2008, the disclosure, subject matter and contents of which are incorporated herein by reference in its entirety.

BACKGROUND OF THE INVENTION

1. Field of the Invention

This invention relates generally to an orthotic device, and particularly to an orthotic that provides adjustable control of a range of angular motion and interchangeability of supports at a joint of the human body where pivoting normally occurs.

2. Description of the Prior Art

An orthotic is a device, such as a brace or splint, for supporting, immobilizing, or treating muscles, joints, or skeletal parts, which are weak, ineffective, deformed, or injured. To assist in restoring a joint of the human body to normal, effective function, the joint may be restricted for a period by an orthotic, which imposes a fixed pivoting position. Or, an orthotic may permit adjustable angular displacement of the joint, which is retained for a period by the orthotic and gradually increased at intervals to improve the pivotal range of use.

A need exists for an orthotic that can be adjusted without removing it from the body to provide proper support while walking, and having interchangeability of suitable replacement supports, via connecting and disconnecting members, for mobile and immobile patients.

SUMMARY OF THE INVENTION

An orthotic having a hinge device for a joint of the human body, at which a body part pivots, includes first and second hinge members able to extend along respective posterior portions of body parts near the joint. The second hinge member is able to be fitted with alternate orthotic support portions. A hinge connection joins the first member and the second member, permitting angular motion about an axis, and mutual disconnection and reconnection of the members at the hinge connection as the second member pivots relative to the first member.

The orthotic is manufactured from lightweight materials, e.g., aluminum and plastic, which are formed by conventional techniques and at low cost. The aluminum may be roll formed or forged, and the plastic may be molded.

Notably, the orthotic device can also include an upper support member attached to an upper support. In turn, the upper support member is adjustably attached to one end of the first hinge member, which is then attached to the second hinge member at an opposite end of the first member, to provide multiple ranges of pivotal movement about respective spaced axes.

A lower support especially suited for use while walking and secured to the second member can be disconnected from the first member by pivoting the second member about a hinge axis to a retracted position and sliding the second member laterally away from the first member. Further, a second lower support, especially suited for use with a shoe or while the user is in bed, and secured to a functionally identical, replacement-second member, can be connected to the first member by sliding the replacement-second member into position at the hinge axis and pivoting said replacement-second member and its second lower support to an extended position. In the extended position, the replacement-second member and its support are mechanically engaged with the first member, preventing their removal until the replacement-second member is again pivoted to the retracted position.

The scope of applicability of the preferred embodiment will become apparent from the following detailed description, claims and drawings. It should be understood, that the description and specific examples, although indicating preferred embodiments of the invention, are given by way of illustration only. Various changes and modifications to the described embodiments and examples will become apparent to those skilled in the art.

DESCRIPTION OF THE DRAWINGS

Having generally described the nature of the invention, reference will now be made to the accompanying drawings used to illustrate and describe the preferred embodiments thereof. Further, these and other advantages will become apparent to those skilled in the art from the following detailed description of the embodiments when considered in light of these drawings in which.

DESCRIPTION OF THE PREFERRED EMBODIMENT

Figure 1:
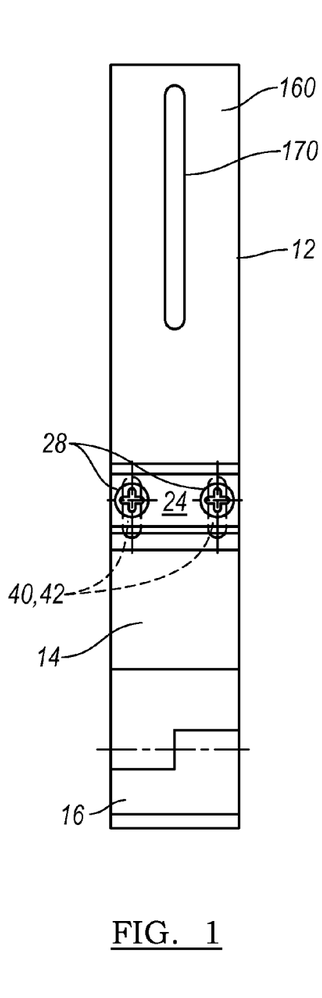
FIG. 1 is a rear view of a hinge device for a joint of an orthotic.
Figure 2:
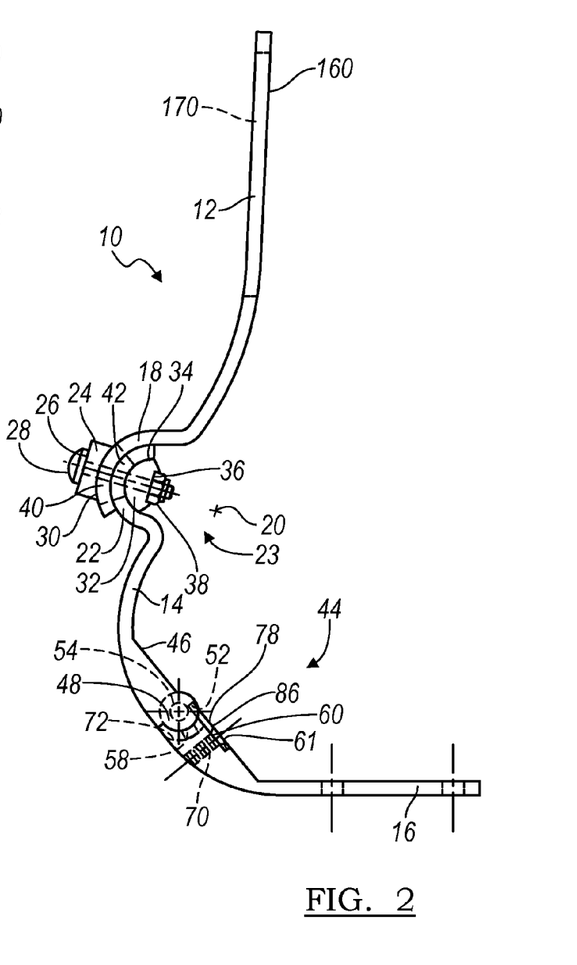
FIG. 2 is a side view of FIG. 1.
Figure 3:
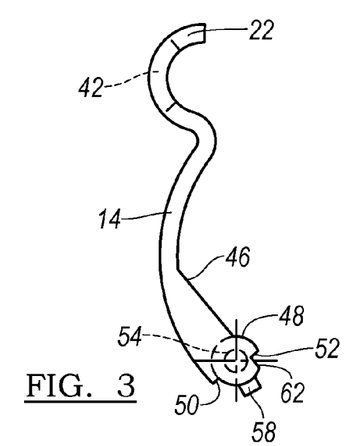
FIG. 3 is a side view of the first hinge member of the device of FIG. 1.

Referring now to FIGS. 1 through 3, an orthotic hinge device 10 for a joint preferably includes an upper member 12, intermediate first hinge member 14, and lower second hinge member 16, each member preferably being of aluminum or another structural material having density, strength and endurance comparable to those of aluminum. Notably, the first hinge member 14 is adjustably attached to an end of the upper member 12, and the second hinge member 16 is hinged at an opposite end of the first member 14.

More specifically, the lower end of the upper member 12 is formed with a circular arc 18 having a center 20. The upper end of the first hinge member 14 is formed with a circular arc 22, which is centered at 20 and whose outer surface nests within the inner surface of arc 18. Members 12 and 14 are connected mutually at an adjustable connection 23. An outer block 24 is formed with a flat outer surface 26, engaged by the head of threaded attachment 28, e.g., a screw or bolt 28, and a circular cylindrical inner surface 30 centered at 20. An inner block 32 is formed with a circular cylindrical outer surface 34 centered at 20, and a flat inner surface 36 contacted by self-locking nuts 38, each nut engaging a respective attachment bolt 28. The upper member 12 is formed with two parallel slotted holes 40. The first hinge member 14 is formed with two holes 42, each hole 42 being aligned with a respective slotted hole 40. Each attachment 28 extends through a hole in the outer block 24, a pair of holes 40, 42 in members 12 and 14, respectively, and a hole in the inner block 32. The lower portion of first member 14 and the upper portion of second member 16 together form an arc that is continuous across a lower hinge connection 44.

Figure 4:
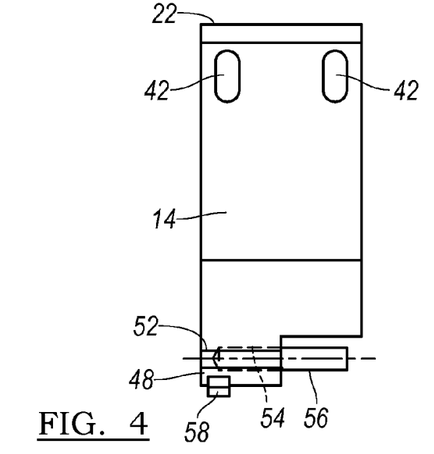
FIG. 4 is a front view of the first member of FIG. 3.

Referring to FIGS. 3 and 4, the inner surface of the first hinge member 14 includes a planar surface 46, which terminates at a cylinder 48 extending laterally about one-half of the width of member 14. The cylinder 48 is formed with an outer stop surface 50 and an inner stop surface 52, which extend along the cylinder's length, which is about 0.750 inch. A blind hole 54 formed in cylinder 48 receives a hardened, anodized stainless steel hinge pin 56 retained in hole 54 with a press fit. A portion of the length of pin 56 extends laterally from the hole. A locking projection 58 is an extended uniform projection, spaced about 0.10 inch from the nearest edge of member 14 and directed radially from the center of hole 54, and extends laterally about 0.187 inch along the length of cylinder 48.

Figure 5:
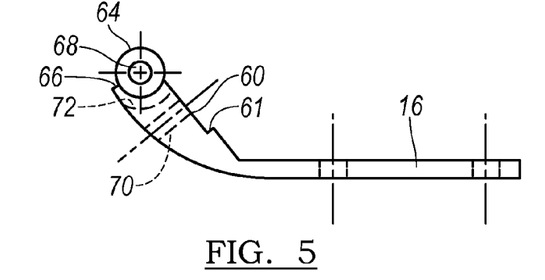
FIG. 5 is a side view of the second hinge member of the device of FIG. 1.
Figure 6:
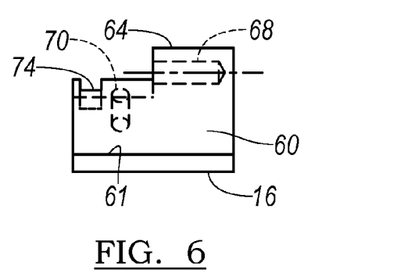
FIG. 6 is a front view of the second member of FIG. 5.
Figure 7:
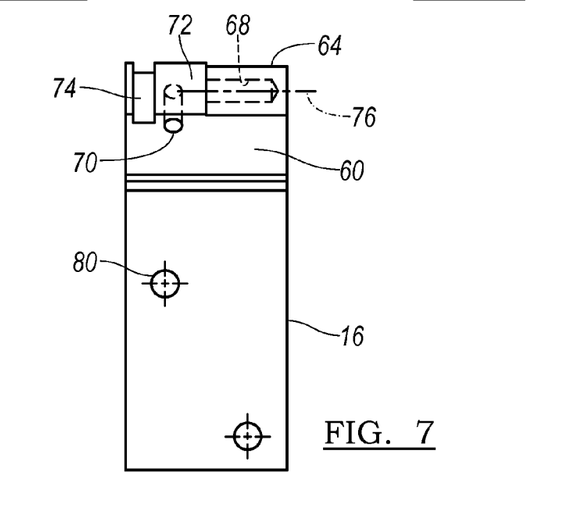
FIG. 7 is a bottom view of FIG. 5.

FIGS. 5-7 illustrate details of the lower, second hinge member 16. The inner surface of the second member 16 includes a planar surface 60, which is substantially coplanar with the surface 62 at the base of the stop surface 52 when the lower connection 44 is extended or open, as shown in FIG. 2. Planar surface 60 terminates at a stop surface 61. A cylinder 64 is aligned with cylinder 48 and extends laterally about one-half of the width of member 16. Cylinder 64 is formed with an outer stop surface 66, which extends along the length of cylinder 64 and is located and sized to contact surface 50 when the lower connection is in the extended position of FIG. 2. A blind hole 68 formed in cylinder 64 is sized to receive the portion of hinge pin 56 that extends laterally from cylinder 48.

A tapped hole 70 is formed through the thickness of the second member 16 between its outer arcuate surface and its planar surface 60.

The second hinge member 16 is formed also with a concave cylindrical surface 72, complementary to the outer convex surface of cylinder 48. Concave cylindrical surface 72 is located and sized to receive cylinder 48 therein. A rectangular groove 74 is formed through the rear surface of concave cylindrical surface 72 and is sized and located to receive therein the locking projection 58 that extends from cylinder 48 of the first hinge member 14, thereby forming a preferred locking mechanism between the first and second members 14, 16, respectively.

In the alternative, of course, the hinge pin 56 may be secured to either member 14 or 16. And, projection 58 may be formed on member 16 and groove 74 may be formed on member 14.

Figures 8A, 8B:
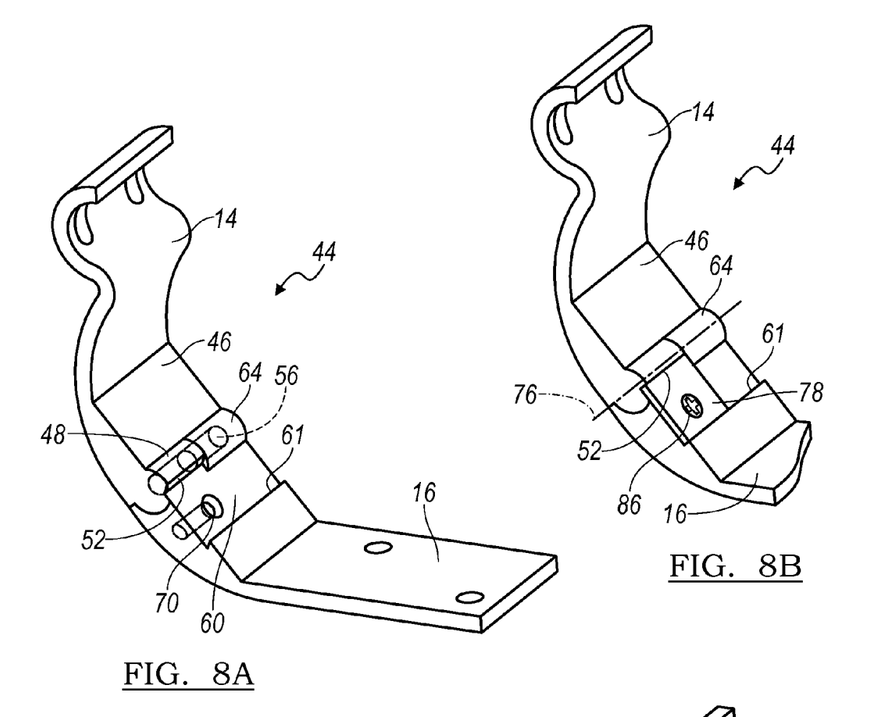
FIG. 8A is a perspective view showing the first and second members assembled and in the extended position without the lockout plate.
FIG. 8B is a perspective view showing the first and second hinge members of the device assembled in the extended position with a lockout plate installed.
Figure 9:
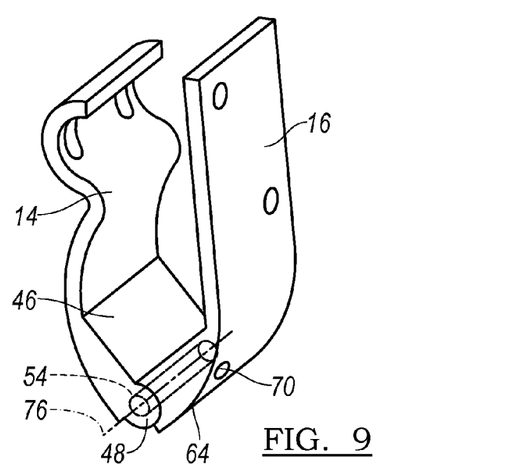
FIG. 9 is a perspective view showing the first and second members assembled and in the retracted position.

In operation (with reference to the preferred embodiment), when the lower connection 44 is closed, or retracted from the extended position shown in FIG. 8A, by rotating the second member 16 counterclockwise relative to the first hinge member 14 as shown in FIG. 9, hinge pin 56 can be inserted into the blind hinge pin hole 68 in cylinder 64 of the second hinge member 16, thereby allowing cylinder 48 of the first hinge member 14 to enter the concave surface 72, and locking projection 58 to become laterally aligned with rectangular groove 74.

Thereafter, when the lower connection 44 is extended to the position shown in FIG. 8A by rotating the second member 16 clockwise about axis 76 relative to the first hinge member 14, locking projection 58 enters, engages and becomes retained in groove 74, thereby securing the second member 16 to the first member 14. More specifically, while projection 58 is engaged with groove 74, the second member 16 is prevented from becoming disconnected from the first member 14. The second member 16 can be disconnected from the first member by rotating the second member counterclockwise to the retracted position shown in FIG. 9, thereby disengaging the locking projection 58 from rectangular groove 74, and slipping the hinge pin 56 out of cylinder 64 by moving the second member laterally relative to the first member 14.

Figure 10:
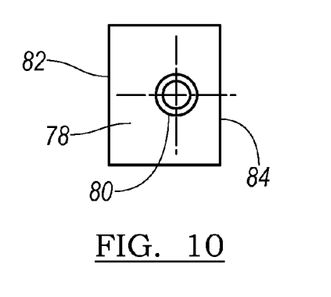
FIG. 10 is a plan view of a rectangular lockout plate.

FIG. 10 shows a flat, rectangular hinge lockout plate 78 formed with a countersunk hole 80 and lateral edges 82, 84 at opposite sides of the plate. When the lower connection 44 is extended to the position shown in FIG. 8A, rotation of the second member 16 relative to first member 14 about axis 76 is prevented by inserting lockout plate 78 into the recessed section formed by aligned planar surfaces 60, 62 such that opposite edges 82, 84 of plate 78 contact the stop surface 52 on the first hinge member 14 and the stop surface 61 on the second hinge member 16. In this position, the hinge plate is secured to the lower connection 44 of the orthotic hinge device 10 by inserting a threaded fastener 86 into the hole 80 and engaging the fastener with the tapped hole 70, as shown in FIGS. 2 and 8B.

Figure 11:
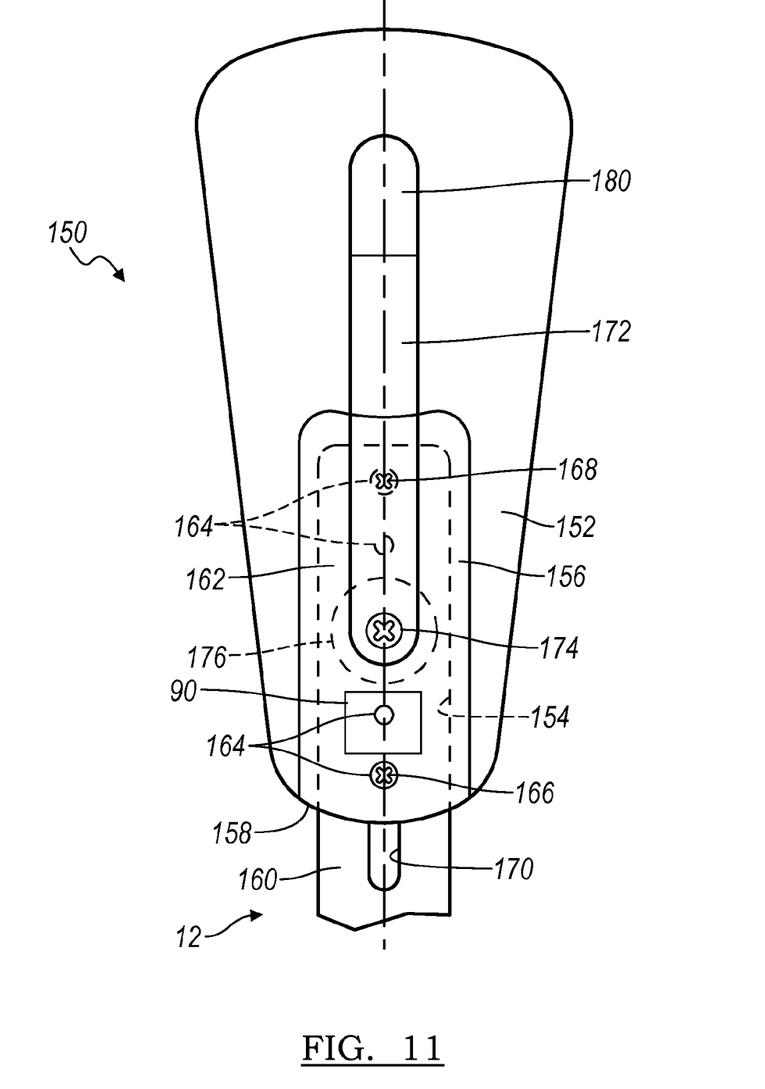
FIG. 11 is a rear view of an upper leg support, into which the orthotic device of FIGS. 1 and 2 can be inserted and retained.
Figure 12:
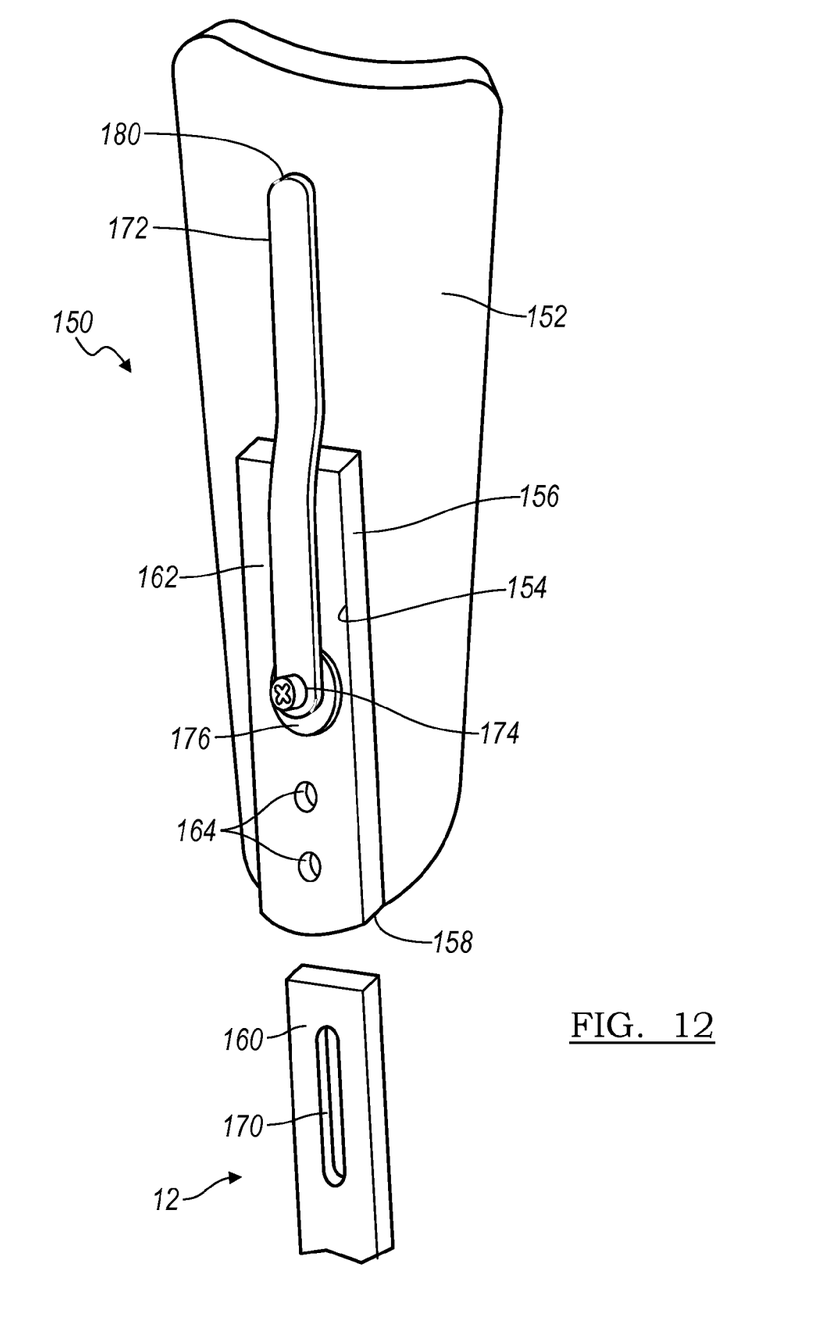
FIG. 12 is a perspective view of the leg support of FIG. 11 aligned for assembly.

FIGS. 11 and 12 show an upper calf support 150, which includes a front or inner surface that conforms to the contour of the calf of the human leg, and an outer surface 152, which is substantially parallel to its inner surface. The outer surface 152 is formed with a hollow pocket 154 enclosed by a wall 156 and having an opening 158, into which the upper end 160 of the upper member 12 is inserted. The outer surface 162 of the pocket 154 has a series of holes 164, which extend through the pocket 154 and the inner and outer surfaces of the upper support 150. Threaded attachments 166, 168, inserted through at least some of the holes 164 and through a slotted hole 170 in the upper member 12, secure the upper support 150 and upper member 12 in a desired position.

When the orthotic hinge device 10 is not being locked in the extended position, the rectangular hinge lockout plate 78 and its threaded fastener 86 can be removed from their secured position in the lower connection 44 and retained on the upper support 150 by inserting plate 78 in a recess 90 formed in the rear surface of the upper support and engaging threaded fastener 86 with the plate, via hole 80 and the corresponding tapped hole 164 in the recess 90 in the support.

A rotating bar 172, in the form of a thin elongated plate, is secured at one end by an attachment 174 to a boss 176 formed on the outer surface 162 of pocket 154. When the rotating bar 172 is not in use, the opposite end 180 of the rotating bar 172 bears against the outer surface 152 and is held in place as shown in FIG. 11. The rotating bar 172 can be rotated in either direction about attachment 174 from the position shown in FIG. 11, such that the area of the rotating bar near its end 180 contacts a surface, e.g., the surface of a bed in which the user is lying, to prop the foot against rotation from the desired position.

Figure 13:
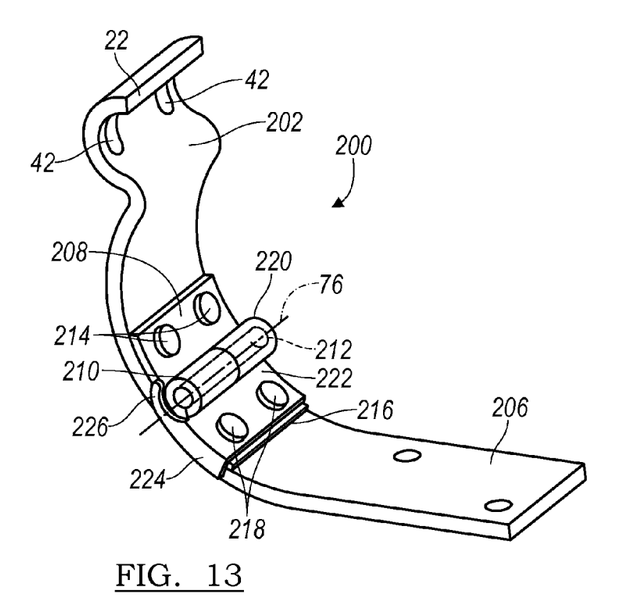
FIG. 13 is a perspective view of an alternative embodiment of the joint device showing alternative first and second hinge members assembled and in the extended position.
Figure 14:
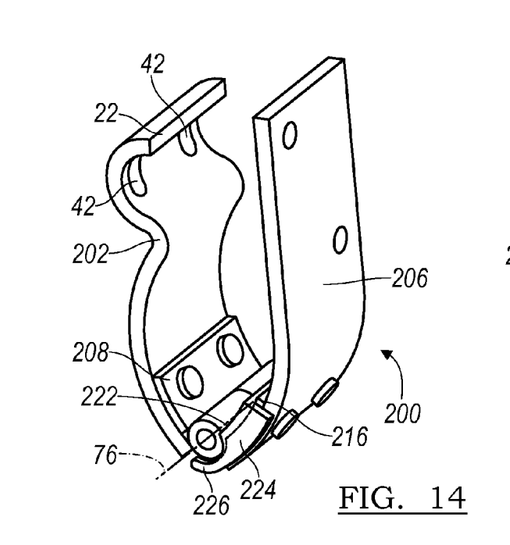
FIG. 14 is a side view showing the alternative first and second members of FIG. 12 assembled and in the retracted position.
Figure 15:
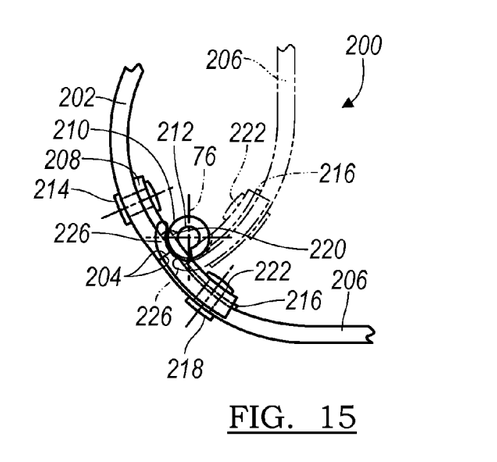
FIG. 15 is a partial side view of the embodiment of FIGS. 13 and 14 showing the members assembled and in the extended position.

As an alternative to lower hinge connection 44, FIGS. 13, 14 and 15 illustrate a second embodiment, i.e. lower hinge connection 200. In this alternative design, a first member 202 terminates at its lower end with a planar contact surface 204, which abuts a planar contact surface 204 at an upper end of a lower second member 206 (best seen in FIG. 15) when the hinge connection 200 is in the extended position shown in FIG. 13. The angular pivotal displacement of the second member 206 in the extended position, i.e. relative the first member 202, is, therefore, limited by contact between surfaces 204.

Further, regarding lower hinge connection 200, a first hinge plate 208 is formed with a cylinder 210, which extends laterally about one-half of the width of the lower connection 200. Cylinder 210 is formed with a central, hinge pin hole aligned with axis 76 and sized to receive therein a length portion of a hinge pin 212 that extends laterally from another cylinder 220. Hinge plate 208 is secured by rivets 214 to the first member 202.

A second hinge plate 216 is secured to the second member 206 (as described below) and is formed with a second cylinder 220, which extends laterally about one-half of the width of the lower connection 200. Cylinder 220 surrounds and retains a hardened, anodized stainless steel hinge pin 212, which is aligned with the hinge axis 76. A portion of the length of hinge pin 212 extends laterally from an inner end of cylinder 220.

Finally, in the locking mechanism of this alternative embodiment, a locking member 222 is secured by rivets 218 above the second hinge plate 216, with rivets 218 passing though and securing it to the second hinge plate 216 and second member 206 as seen in FIG. 15. Specifically, the locking member 222 overlaps the face of second hinge plate 216 and includes a locking arm or projection 224, and the locking projection in this case overlaps lateral side edges of the first and second members 202, 206, respectively (i.e. adjacent the contact surfaces 204 of lower connection 200 when in the extended position as shown in FIGS. 13 and 15). The locking arm 224 has a hooked end 226 with an arcuate profile, whose radial inner surface is substantially coaxial with axis 76 and is sized to surround the outer surface of cylinder 210.

In operation (i.e. to disconnect and reconnect first and second members 202, 206, respectively), with the lower connection 200 closed, or retracted from the extended position shown in FIG. 13 (by rotating second member 206 counterclockwise relative to first member 202 as shown in FIG. 14), cylinder 210 can pass through the arcuate profile and hook 226 as the second member 206 is moved laterally along hinge axis 76. Notably, when reconnecting, hinge pin 212 becomes inserted into the hinge pin hole in cylinder 210 of the first member 202 until the inner end of cylinder 210 of the first member 202 abuts the inner end of cylinder 220 of the second member 206, to form the hinge joint of lower connection 200.

Thereafter, when the second member 206 is rotated relative to first member 202 clockwise about axis 76 to the extended position shown in FIG. 13, the hook 226 rotates to a position where it overlaps the outer lateral surfaces of the first member 202 and the first hinge plate 208, thereby securing the lower second member 206 to the first member 202. While hook 226 overlaps the outer lateral surfaces of the first member 202 and the first hinge plate 208, lateral movement of the first member 202 tending to disconnect the lower connection 200 causes the inner surface of the hook 226 to contact the first member 202 and the first hinge plate 208, preventing the disconnection.

To disconnect the second member 206 from the first member 202, the second member 206 is rotated counterclockwise to the retracted position shown in FIG. 14, thereby rotating hook 226 away from overlapping the outer lateral surfaces of the first member 202 and the first hinge plate 208. Then, the first member 202 slides laterally away from the second member, disconnecting hinge pin 212 from cylinder 210.

It is important to note that, alternatively, the hinge pin 212 may be secured to the first cylinder 210 and extends toward the second cylinder 220, and the locking arm 224 and hook 226 may be located at the opposite lateral side of the second member 206 from the location shown in FIGS. 13-15. In another option, the locking member 222, locking projection 224 with hook 226 may be secured to the first member 202, such that these components 222, 224, 226 can be located on either lateral side of member 202.

Figure 16:
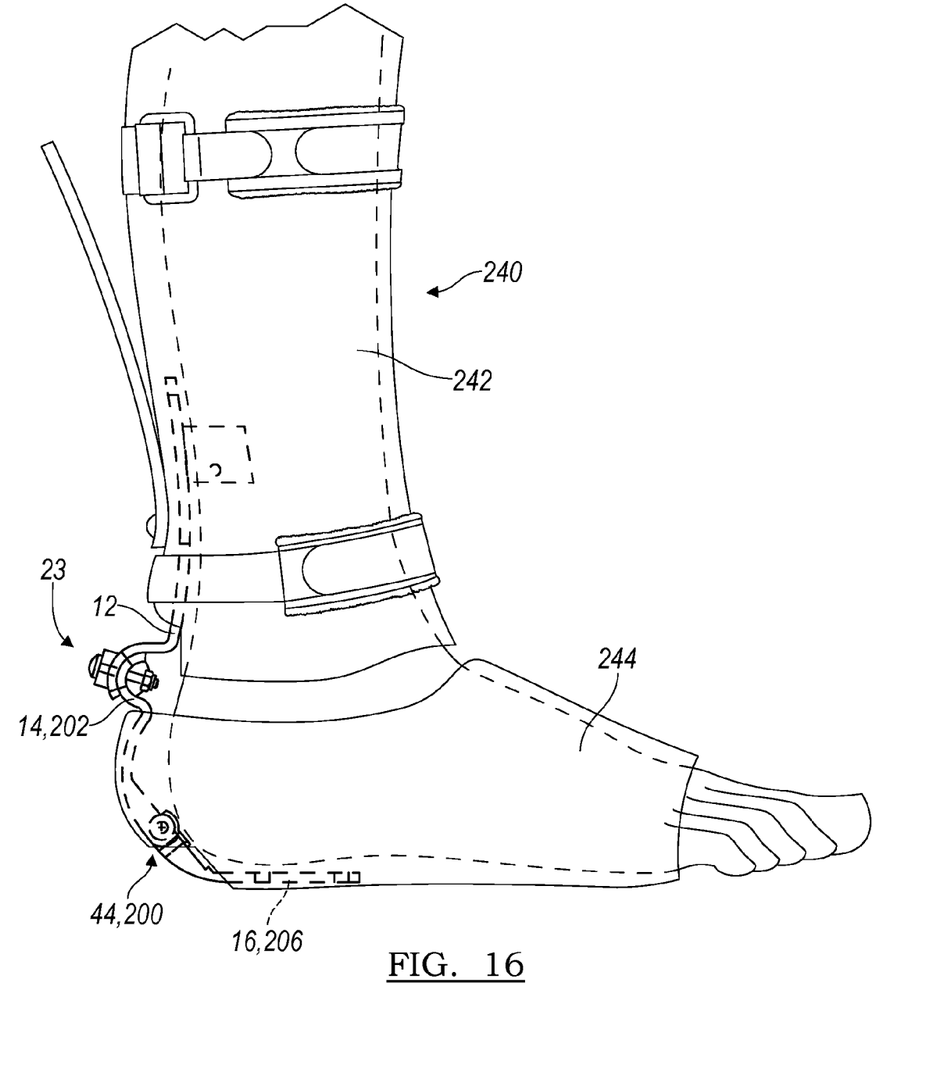
FIG. 16 is a side elevational view of an assembled orthotic positioned on a patient, wherein the orthotic includes the hinge device of the invention for a joint with the second member attached to a bone cast as a lower support.

The adjustable connection 23 and hinge connections 44, 200 can be used in various therapeutic treatment situations with interchangeable upper and lower supports, such as with a typical leg cast for the treatment of broken bones, as seen in FIG. 16. The custom cast 240 for the immobilization of a patient's leg, allowing the healing of broken bones, can be formed by use of either hinge connections 44, 200, although hinge connection 44 is preferred. In the example chosen for illustration, the custom cast 240 is formed about and on the patient's leg after the bone has been set. The bone cast 240 is typically formed by building up multiple layers of fabric material saturated with a hardening medium, such as plaster of Paris. As the bone cast 240 is formed, the orthotic hinge device 10 with adjustable connection 23 is incorporated to provide an adjustable relationship between an upper leg bone cast support 242 and a lower foot bone cast support 244. Second member 16, which extends from the preferred hinge connection 44, is secured to the foot cast support 244.

Figure 17:
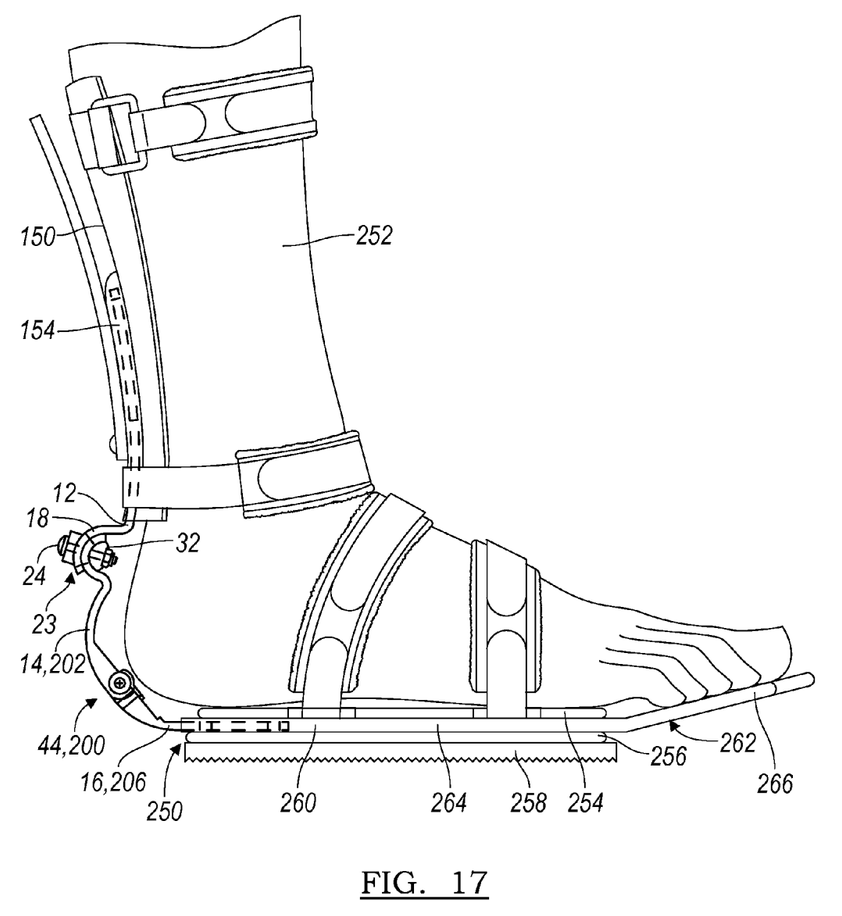
FIG. 17 is a side elevational view of the assembled orthotic positioned on the patient, wherein the second member is attached to an open, foot portion with a walking base used for limited mobility as the lower support.

FIG. 17 illustrates another application of an orthotic hinge device 10 that includes adjustable connection 23 and hinge connection 44, 200 for use by a patient while in bed or with limited mobility. The orthotic shown in FIG. 17 includes a lower foot support 250 attached to the second member 16, 206; an upper calf support 150 attached to the upper member 12; and a heel portion which includes first member 14, 202 intermediate to and interconnecting members 12 and 16 (or 206 with reference to first member 202). The upper calf support 150 and lower foot support 250 are made of synthetic plastic resin, so that they can be molded or pre-formed to the desired contours with various shapes required for engagement with a patent's leg 252. Upper calf support 150' shown in FIG. 18, for example, restricts mobility of the patient's calf more than upper support 150 shown in FIG. 17, in order to secure the patient's leg and foot while walking.

The foot support 250 includes a foot pad 254 connected to a generally rectangular attachment base 256, which has a resilient walking pad 258 secured to its lower surface. The foot pad 254 is also of a generally rectangular configuration. A mounting pocket 260 extends inwardly from the bottom of the foot pad 254 for engagement of the second member 16, 206 between the foot pad 254 and the abutting attachment base 256. A toe extension member 262 can be adjustably secured to the foot pad 254 opposite mounting pocket 260. The toe extension member 262 has a flat base area 264 with an upturned angular offset end portion 266, whose length is sufficient to support a bed sheet and blanket above the patient's toes while wearing the orthotic in bed. The toe extension member 262 is attached between the foot pad 254 and the attachment base 256 by a mounting slot and adjustable fasteners, which extend from the foot pad 254 through the attachment base 256 allowing for lengthening of the overall foot portion 250.

Figure 18:
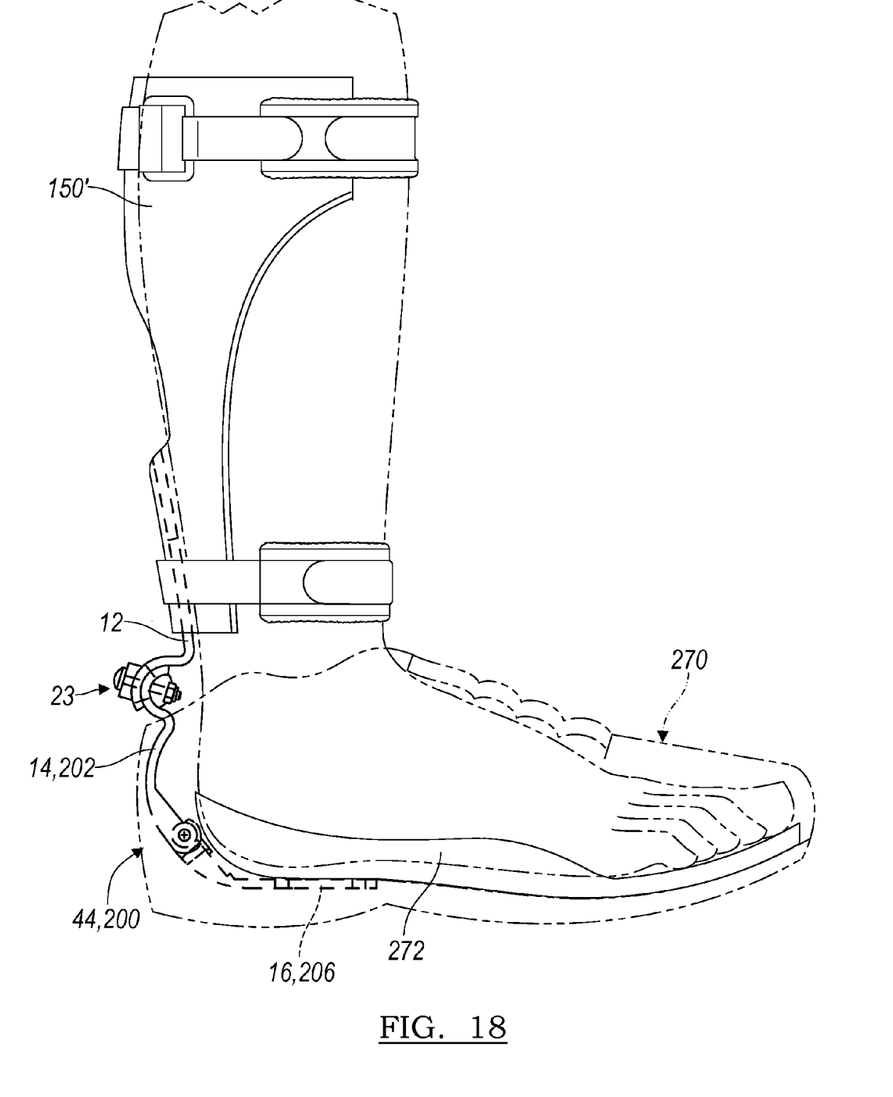
FIG. 18 is a side elevational view of the assembled orthotic positioned on the patient, wherein the second member of the hinge device is attached to a sole insert to wear with a shoe for more advanced mobility than the configurations depicted in FIGS. 16 and 17.

FIG. 18 illustrates yet another orthotic that includes the orthotic hinge device 10, with adjustable connection 23 and hinge connection 44, 200 for use by a patient while walking. In this case, second member 16, 206 extends from hinge connection 44, 200 into a modified shoe 270, shown in broken lines of FIG. 18. The second member 16, 206 in this case is preferably connected to a sole insert 272 as the lower support formed to conform to the shape of the patient's foot. The orthotic of FIG. 18 provides structural continuity and support between the patient's calf and foot. Notably, it is not necessary to include the rotating bar 172 with this configuration since this arrangement is primarily intended to control lateral movement of the leg relative to the foot while walking. In other words, it, unlike the orthotics of FIGS. 16 and 17, is not intended to be worn in bed where control of leg and foot rotation is desired.

Of course, many other upper and lower supports can be used with this invention. Notably, this invention allows for interchangeability or replacement, via the quick and easy disconnecting and reconnecting of the hinge connection 44, 200, so that any of the various upper supports (e.g., calf supports 150, 150', 242) can be fitted with any one of the many lower supports (e.g., foot supports 244, 250, 272), to best treat the patient's immediate and/or long-term condition and rehabilitation protocol.

It should be noted that the present invention can be practiced to treat any of the several joints of the human body and is not limited to the foot and ankle as specifically illustrated and described herein. Further, the present invention may be embodied in other specific forms without departing from its spirit or scope. It is intended that all such modifications and alterations be included insofar as they are consistent with the objectives and spirit of the invention. All changes that come within the meaning and range of equivalency of the claims are to be embraced within their scope.

What is claimed is:

1. An orthotic hinge for a joint of a human body at which a body part pivots, comprising:
    first and second members able to extend along respective posterior portions of body parts near the joint, each member able to be fitted with alternate orthotic support portions;
    an angular adjustment connection joining one of the first member and the second member to a third member to provide an adjustable range of angular motion between the third member and said joined first or second member, the third member having an arcuate shape centered at an adjustment axis, and the joined first or second member having an arcuate shape centered at the same adjustment axis overlapping the arcuate shape of the third member, and an attachment for permitting the arcuate shapes to rotate about the adjustment axis, and for mutually securing the third member and joined first or second member; and
    a hinge connection joining the first member and the second member, permitting angular motion about a hinge axis, and mutual disconnection and reconnection of the first and second members along the hinge axis, the hinge connection further comprising:
        a first hinge plate secured to the first member, including a first cylinder with a hinge pin centered at the hinge axis and extending laterally from the first cylinder;
        a second hinge plate secured to the second member, including a second cylinder having a hole sized and aligned to receive the hinge pin therein;
        the hinge pin secured to the first member, interconnecting the first member and the second member, permitting the first member to pivot relative to the second member; and
        a locking mechanism having a locking projection extending from said one of the first member and the second member, the locking projection engageable with the other member of the first member and the second member, wherein the locking projection prevents disconnection of the hinge pin from the other member of the first member and the second member when the hinge connection is pivoted to an extended position, and wherein the locking projection disengages the other member of the first member and the second member when the hinge connection is pivoted to a retracted position.

2. The orthotic hinge of claim 1, wherein:
    the second member includes the locking projection which at least partially overlaps a lateral surface of the first member when the hinge connection pivots to the extended position; and
    the locking projection moves when the second member is pivoted, from overlapping the lateral surface of the first member to permit the second cylinder to disconnect from the first cylinder when the hinge connection is in the retracted position.

3. The orthotic hinge of claim 1, wherein the locking projection is formed with a hook.

4. An orthotic device for a joint of a human body at which body parts pivot, comprising:
    an upper support and a lower support, each support able to extend along respective posterior portions of said body parts near the joint; and
    a hinge connection joining a first member and a second member, permitting angular motion about a hinge axis and mutual disconnection and reconnection of the first and second members at the hinge connection, the second member able to be fitted with alternate orthotic lower supports, and the hinge connection having:
        a hinge pin secured to one of the first member and the second member;
        a locking mechanism including a locking projection that prevents mutual disconnection of the first member and the second member when the hinge connection is pivoted to an extended position, and that permits mutual connection of the first member and the second member when the hinge connection is pivoted to a retracted position;

a first hinge plate secured to the first member, the first hinge plate including a first cylinder, the hinge pin being centered at the hinge axis; and a second hinge plate secured to the second member, the second hinge plate including a second cylinder aligned to receive the hinge pin therein; and wherein the locking mechanism includes the locking projection secured to one of the first member and the second member, the locking projection located to engage a surface of at least one of the other of the first member and the second member when the hinge connection pivots to the extended position, and wherein the locking projection permits the second cylinder to disconnect from the first cylinder when the hinge connection pivots to the retracted position; and an adjustment mechanism having a first surface located on the first member and formed in a first arc centered at an adjustment axis, the first arc having a first slotted hole extending along the first arc, and a second surface located on a third member, the second surface formed in a second arc centered at the adjustment axis overlapping the first arc, said second surface having a second slotted hole extending along the second arc aligned with the first slotted hole, and an attachment that extends through the first and second slotted holes for permitting the first surface and the second surface to rotate about the adjustment axis, and for mutually securing the first surface and the second surface.

5. The orthotic device of claim 4, wherein:

the locking projection having an arm located to overlap a lateral surface of at least one of the other of the first member and the second member when the hinge connection pivots to the extended position; and the arm permits the second cylinder to disconnect from the first cylinder when the hinge connection pivots to the retracted position.

6. The orthotic device of claim 4, wherein:

the second member includes the locking projection which engages a lateral surface of the first member to prevent removal of the second cylinder from the hinge pin when the hinge connection is pivoted about the hinge axis to the extended position, and the locking projection disengages the lateral surface of the first member so that the second cylinder is removable from the hinge pin when the hinge connection is pivoted about the hinge axis to the retracted position.

7. The orthotic device of claim 4, wherein:

the locking projection having an arm located adjacent a lateral surface of the second member when the hinge connection is in the extended position; and the arm permits the second cylinder to disconnect from the first cylinder when the hinge connection is pivoted to the retracted position.

* * * * *